United States Patent [19]

Peyton et al.

[11] 3,975,260

[45] Aug. 17, 1976

[54] BOTTLE HANDLING APPARATUS

[75] Inventors: John J. Peyton; James H. Wyman, both of Santa Barbara, Calif.

[73] Assignee: Industrial Automation Corporation, Santa Barbara, Calif.

[22] Filed: Oct. 23, 1973

[21] Appl. No.: 408,921

Related U.S. Application Data

[63] Continuation of Ser. No. 305,708, Nov. 13, 1972, abandoned.

[52] U.S. Cl. .......................... 209/73; 209/111.7 T; 198/22 B; 198/210
[51] Int. Cl.² .......................................... B07C 5/342
[58] Field of Search ................ 209/74 R, 73, 111.7, 209/75; 198/210, 22 B

[56] References Cited
UNITED STATES PATENTS

| | | | |
|---|---|---|---|
| 1,211,611 | 1/1917 | Meyer et al. | 198/22 B |
| 1,885,377 | 11/1932 | Robinson | 294/115 X |
| 3,175,705 | 3/1965 | Honda, Jr. | 294/115 X |
| 3,710,928 | 1/1973 | Zijp | 198/210 |

*Primary Examiner*—Allen N. Knowles
*Attorney, Agent, or Firm*—Spensley, Horn, & Lubitz

[57] ABSTRACT

Improvements in bottle handling apparatus whereby bottles may be firmly grasped by the neck thereof for conveying but may be easily and quickly released as desired. A pair of spaced elongated members, somewhat flexible by design, extend outward adjacently and are manipulated to clamp and retain the bottles. The elongated members are pivotally supported intermediate the ends thereof and a toggle joint mechanism is disposed to spread the rear portion of the elongated members so as to cause the forward portion thereof to grasp a bottle. A spring across the toggle mechanism drives the clamp into either the completely open or completely closed position in response to an impulse. Mechanism is provided for causing the clamp to release at one of a plurality of possible locations depending on the desired position of the bottle being conveyed.

38 Claims, 11 Drawing Figures

U.S. Patent  Aug. 17, 1976  Sheet 1 of 3  3,975,260
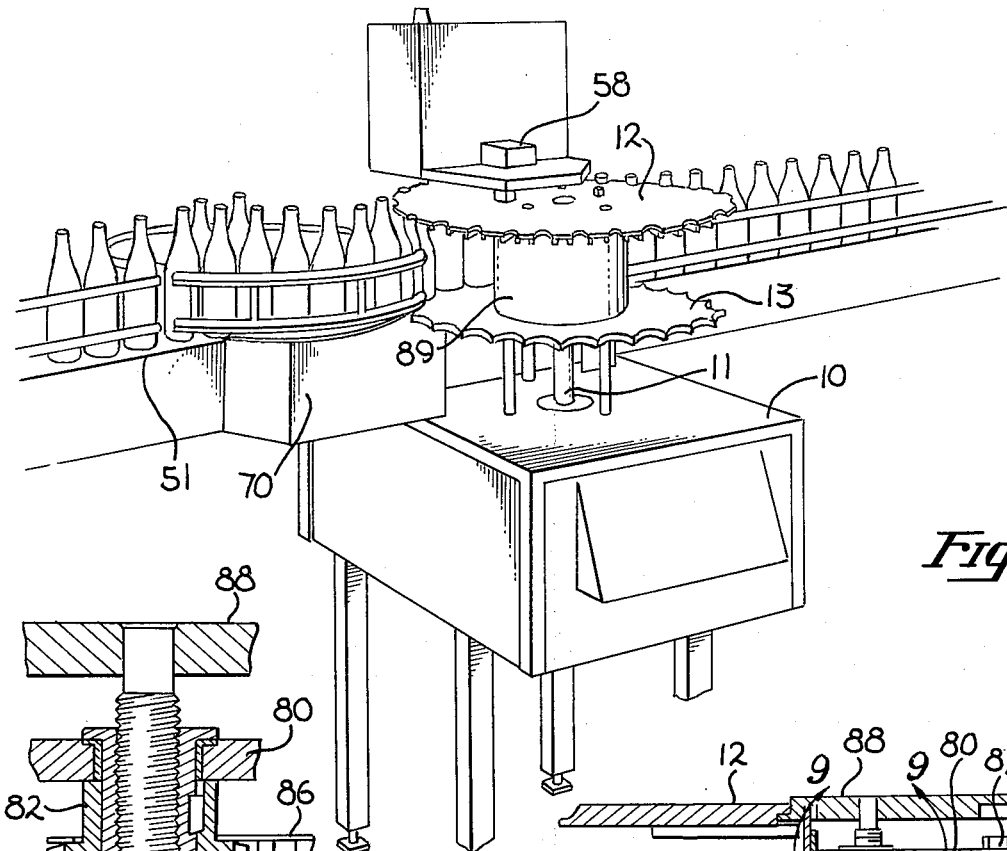
Fig. 1
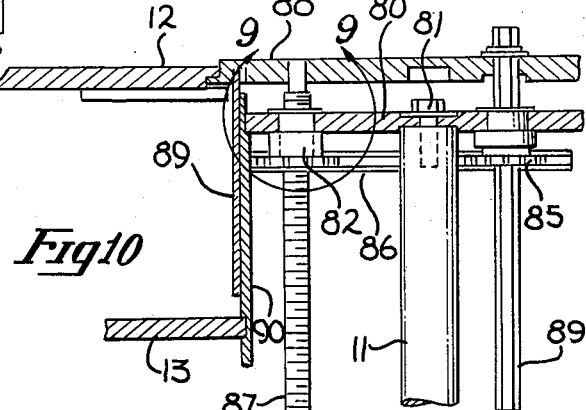
Fig. 9
Fig. 10
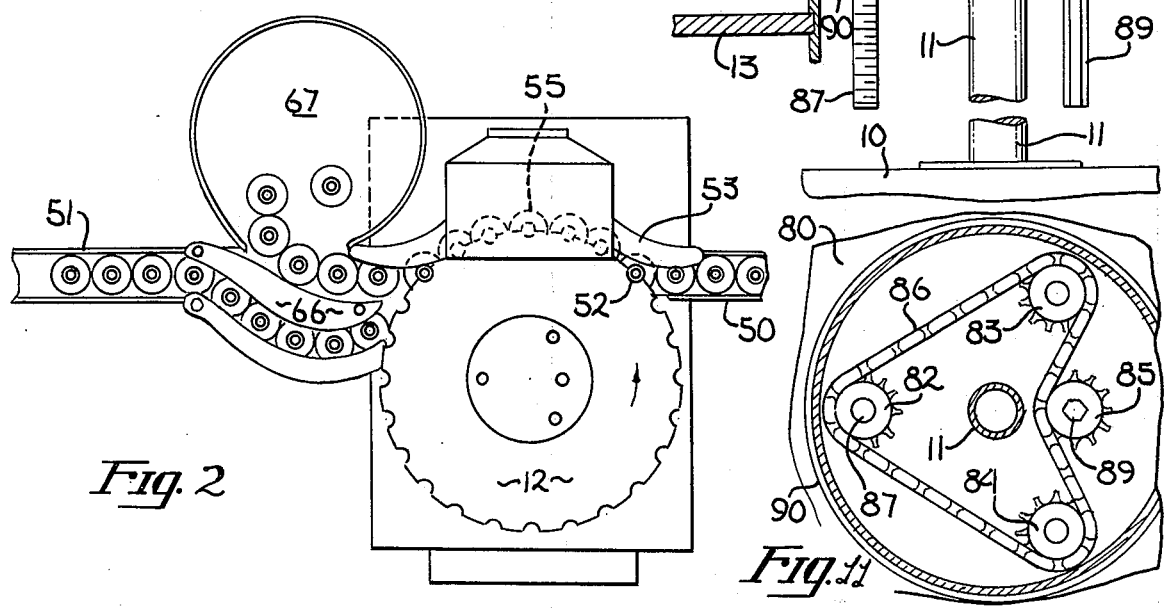
Fig. 2
Fig. 11

BOTTLE HANDLING APPARATUS

This is a continuation of application Ser. No. 305,708, filed Nov. 13, 1972.

BACKGROUND OF THE INVENTION

1. Field of the Invention

The present invention relates to the field of container handling apparatus and more particularly to apparatus for physically grasping, conveying and releasing containers, such as bottles, on command.

2. Prior Art

The present invention is particularly directed to the handling of containers and particularly of bottles in application where the bottles may not be supported from beneath for any of various reasons. As a typical example and as an illustration of the apparatus for which the preferred embodiment of the present invention is specifically adapted to be used, it is well known to inspect bottles prior to the filling thereof with a beverage or other food product by directing an appropriately disposed light through the bottom of the bottle and viewing the inside of the bottle through the neck thereof. The bottles may not be supported from the base even by a transparent support member during the inspection, as dirt located between the support member and the base of the bottle may be interpreted as being located within the bottle itself, thereby causing rejection of a large number of clean bottles. Similarly, the bottles may not be supported from the top for the same reason. Consequently, in such equipment, it is necessary to engage and support the bottles in some manner from the sides thereof during the inspection procedure.

The equipment of the type described hereabove is presently manufactured by Industrial Automation Corporation of Santa Barbara, California, and sold as their electronic bottle inspector. In such equipment, the bottles are delivered by conveyor to a rotating assembly referred to as a starwheel which is adapted to engage the bottles from the sides at a first level adjacent to the top thereof and at a second level adjacent to bottom thereof. At the same time a rubber suction cup type device engages the bottle between the first and second levels and through the appropriate control of a vacuum delivered to the suction cup, the bottles may be retained or released as desired. The starwheel picks up the bottles from a supply conveyor, carries them past an inspection head and delivers the bottles to a delivery conveyor or rejected bottle corral as required. Those bottles which are indicated as being contaminated by the inspection head, are released by the vacuum device before the bottles reach the delivery conveyor, thereby allowing the bottles to progress to the rejected bottle corral rather than to the delivery conveyor.

The suction cup arrangement which performs the desired function and much equipment of the hereabove described design is in every day use. However, there are certain characteristics of such equipment which are in need of improvement. In particular, the suction cups are subject to deterioration and leakage so as to require occasional replacement if the bottles are to be reliably supported over the inspection station. Also, while the environment in which such equipment is used, obviously must be a relatively clean environment, the continued ingress of unfiltered air to the suction cups, valves and small passageways within the apparatus, can result in a buildup of foreign particles interfering with the rapid communication of the vacuum to the suction cup and, similarly, with the rapid vacuum breaking upon venting the particular cup to the atmosphere. Furthermore, since there are a relatively large number of the vacuum cups, valves, etc. on the starwheel, each of the valves must be independently operable and the mechanism for such an assembly is substantial. Furthermore, while the top and bottom portions of the starwheel are split so as to be readily removable for changing to a different starwheel for bottles of a different size, the vacuum system may not be so readily changed. In particular, the entire assembly of suction cups, valves, etc. must be changed to accommodate a new system with a different number of suction cups, valves, etc. Consequently, the change from one bottle size to another is a substantial undertaking and relatively expensive apparatus must be provided in various configurations to accommodate the change in the starwheel.

There is thus a need for improvement in such starwheel to provide a low cost readily changeable means for grasping and supporting bottles from the sides thereof.

SUMMARY

Bottles or other containers are delivered to the apparatus of this invention by a conventional conveyor system which consists essentially of a narrow belt on which the bottles sit as they are being conveyed from one point to another. The conveyor delivers the bottles to a circular carriage, known in the trade as a starwheel, which has a series of recesses in its periphery for receiving the bottles. The starwheel travels with the same peripheral speed as the conveyor and the bottles are retained in the recesses by a guard member which pens the bottles in and a series of clamps, one associated with each recess, which grasp the bottles.

The clamps are actuated by a spring loaded, over center lock, toggle joint mechanism which has two stable positions, open and closed. A cam positioned at an appropriate place closes each clamp as it passes the position where it can receive a bottle from the supply conveyor.

The bottle, thus doubly secured to the starwheel is carried to a station where some operation, as for example inspection, is to be carried out on the bottle. In the particular application of this invention described herein, the bottles are to be inspected for foreign matter before being filled. In this application, the bottle must be suspended and not supported by its base lest foreign matter on the support be interpreted by the inspection circuitry as being within the bottle. In the invented apparatus, the bottles are secured on their sides so that no difficulty ensues in performing the required inspection.

At the inspection station, circuitry which is known to the art and not a part of this invention is provided to ascertain whether or not the bottle being inspected is acceptable. A signal from the inspection circuitry indicates an unacceptable bottle and activates a solenoid which delivers an impulse to the clamp holding that bottle so as to open the clamp. The bottle, being secured by the guard member in addition to the clamp, is unaffected at this point in time and continues travelling with the starwheel to the point at which the guard member no longer secures the bottle in its recess. A fixed guide directs any bottles so released to a rejected bottle corral from which they may be manually removed and reprocessed.

Bottles which are acceptable at the inspection point continue travel with the starwheel secured both by the guard member and the clamp. When the point at which unacceptable bottles are released is reached, acceptable bottles are not released because they are still secured in their recesses by the clamp. These bottles continue with the starwheel to a later point at which a fixed cam releases all clamps which are closed. A guide from this point directs the bottles so released to the output conveyor for transport to the next operation.

BRIEF DESCRIPTION OF THE DRAWINGS

FIG. 1 is a perspective view of a complete apparatus showing bottles being processed through the machine.

FIG. 2 is a top view of the apparatus.

FIG. 9 is a sectional view of the sprocket assembly taken at 9—9 of FIG. 10.

FIG. 10 is a sectional view of the starwheel spacing adjusting mechanism.

FIG. 11 is a top sectional view showing the sprocket drive details of the starwheel spacing adjusting mechanism.

DETAILED DESCRIPTION OF THE INVENTION

Figure 3:
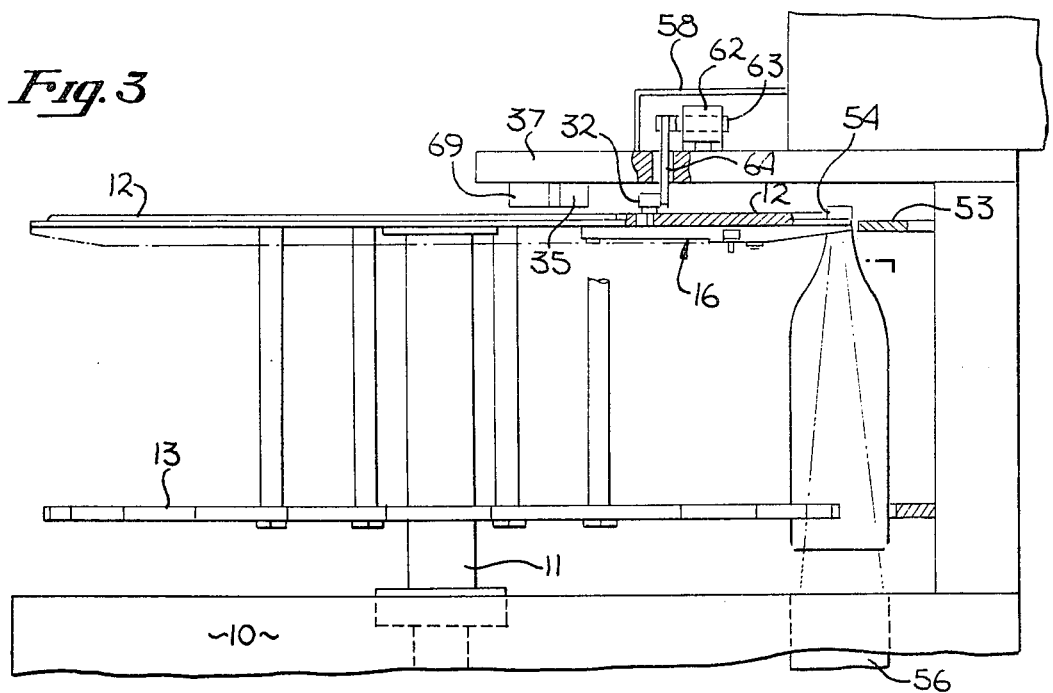
FIG. 3 is a side sectional view detail of the starwheels taken through the inspection station.
Figure 4:
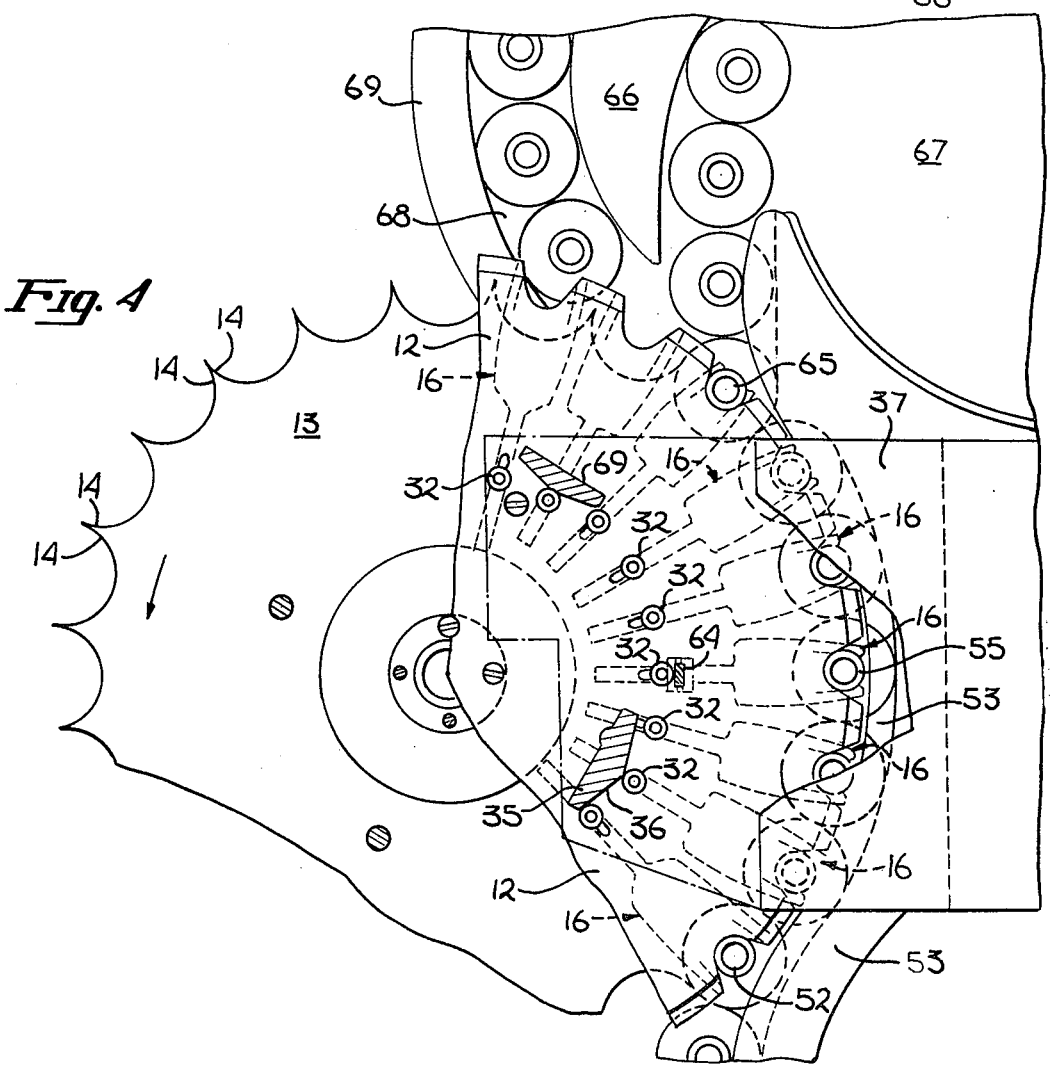
FIG. 4 is a top view partly sectioned detail of the starwheels showing the path of containers through the apparatus.
Figure 5:
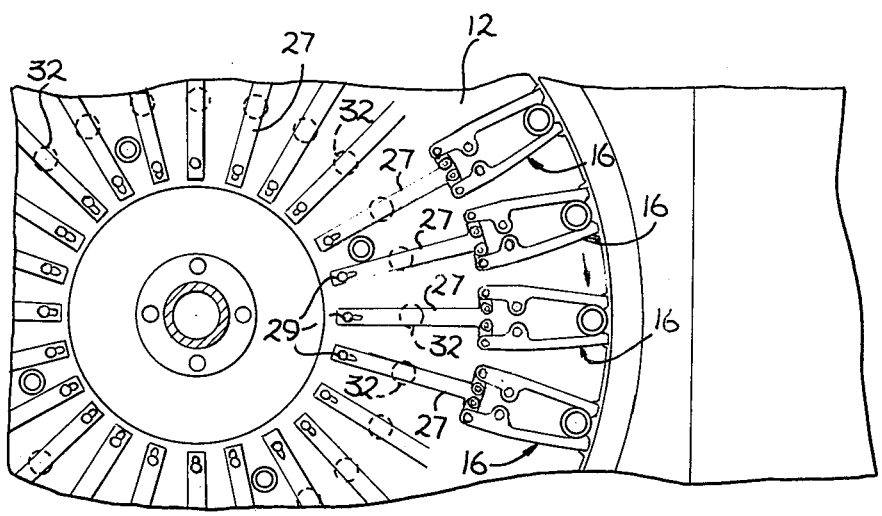
FIG. 5 is an underside view of a portion of the upper starwheel.
Figure 6:
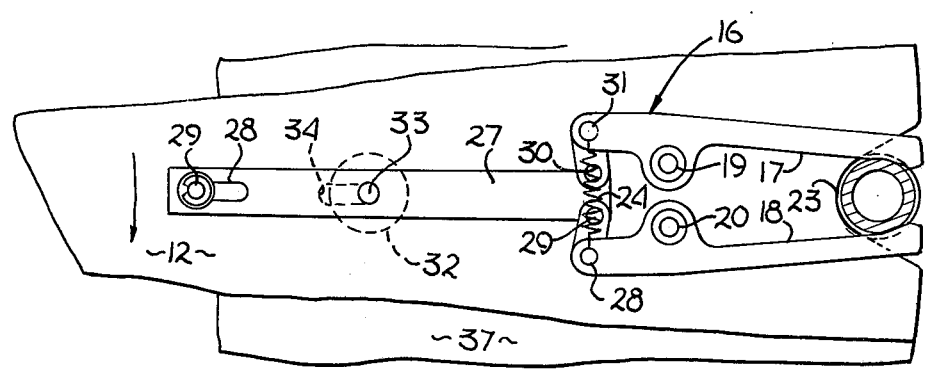
FIG. 6 is a detailed view of a clamp in the closed position.
Figure 7:
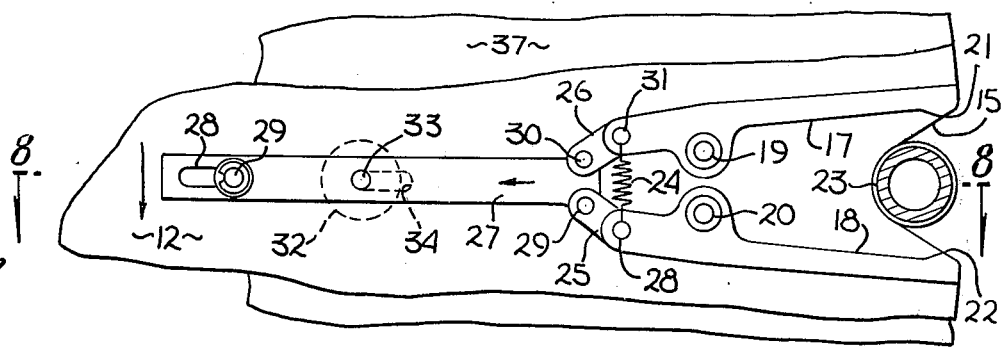
FIG. 7 is a detailed view of a clamp in the open position.
Figure 8:
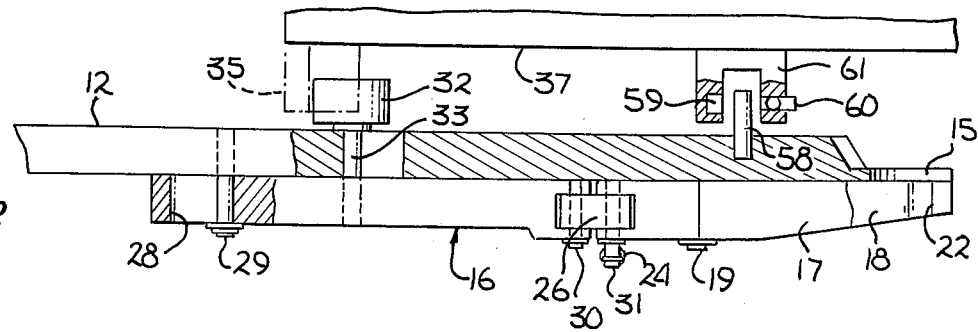
FIG. 8 is a cross sectional view of a clamp taken at 9—9 of FIG. 8.

The illustrated embodiment of the present invention, as shown in FIG. 1 includes a base 10 from which a rotatable shaft 11 protrudes vertically upward. The rotatable shaft 11 carries an upper starwheel 12 and a lower starwheel 13 which function to carry bottles through the machine. The periphery of each starwheel is cut out to receive a number of bottles as can best be seen as recesses 14 and 15 in FIG. 4. Recesses 14 in the lower starwheel are preferably circular in shape and are intended to approximately fit the circumference of the bottles to be inspected. Recesses 15 in the upper starwheel have a generally V-shape with a radius 23 at the root. The radius 23 approximately fits the neck of the bottles to be inspected. The alignment of the starwheels is such that when the neck of a bottle is being held in recess 15 of starwheel 12, the body of the bottle fits the corresponding recess 14 in lower starwheel 13 so that the bottle is held in a substantially vertical position.

The periphery of the upper starwheel 12 is made relatively thin so that short necked bottles can be grasped by a clamp (to be described later) with the beaded portion of the bottle neck above the top surface of the starwheel. Mounted on the bottom surface of starwheel 12 are a series of clamps 16, one corresponding to each recess.

Bottles to be inspected are conveyed to the machine on a conventional conveyor system indicated in FIGS. 1 and 2 by the numeral 50. The supply conveyor 50 places the bottles, serially, into successive recesses of the starwheels. The starwheels are turned by gearing, not shown, coupled to the conveyor 50, so that the peripheral speed of the starwheels is about equal to the surface speed of the conveyor system. A clamp 16 associated with the recess closes around the neck of each bottle as it is presented to the starwheels and the bottle is then carried by the starwheels through the inspection station to a release point beyond the inspection station. Rejected bottles are released at a predetermined point after being inspected from which point they proceed to a corral for rejected bottles, as will be explained in detail later. Acceptable bottles are released at a later time than rejected bottles at a point which allows them to be channeled to an output conveyor 51 driven from the same source and at the same speed as the supply conveyor and the starwheel assembly.

As any particular bottle position on the starwheels approaches the location 52, where it may be presented with a bottle, the clamp 16 associated therewith is in the open position, and a bottle being conveyed on conveyor 50 to the location 52 will be positioned with its neck within recess 15 and its body within recess 14. The conveyor 50 extends to the point that delivers bottles to the position 52 and further motion of the bottles is provided by the rotation of the starwheels which, as previously stated, is geared to the conveyor. As the bottle progresses toward the inspection station, a guard 53 pens the neck of the bottle in recess 15 leaving insufficient space for the beaded top section of the bottle 54 to pass through the opening left, but yet not so tightly that excessive friction is generated.

Clamp 16 also closes around the neck of the bottle, as will be hereinafter explained, also securing the bottle to the starwheels irrespective of guard 53.

Each clamp comprises a pair of gripper arms 17 and 18 pivoted on shoulder screws 19 and 20 screwed into the bottom surface of the starwheel. The gripper arms 17 and 18 are preferably made of a plastic material and are relatively long and thin so as to be slightly flexible. The tips of the gripper arms have inward protrusions 21 and 22 so that when the clamp is closed around the neck of a bottle, the bottle will be held between the arms 17 and 18 and urged against radius 23 allowing the beaded portion of the neck of the bottle to be supported on the top surface of the starwheel 12.

The opening of the mouth of clamp 16 is controlled by links 25 and 26, and actuator 27, which are connected by pivots 28, 29, 30 and 31 making a toggle joint. The limits of travel of the actuator 27 are determined by slot 28 in the actuator and stop 29 which is a shoulder screw screwed into starwheel 12. The travel is set so that when the actuator is retracted the mouth of the clamp 16 is open slightly wider than the opening of recess 15, and when the actuator is in the forward position the toggle joint is slightly over center and the gripper arms 17 and 18 are in the closed position to clamp the neck of a bottle. The effect of spring 24, which is across the toggle joint, is to create a mechanism having two stable states, the spring driving the actuator against one stop or the other depending on which side of center the links happen to be at the moment. Thus the clamp 16 can be either completely open or completely closed by a simple movement of the actuator 27 past the center of the toggle joint motion and spring 24 will hold the clamp in either position without external holding mechanisms.

A cam follower 32, free to turn, is positioned slightly above the top surface of starwheel 12 and secured to actuator 27 by pin 33 which extends through slot 34. Cam 35, having a face 36 inclined at an angle to the path of the cam followers 32 as the starwheels turn, is mounted on overhanging arm 37 which is secured to the base 10 by means not shown. The clamps, which are open as they approach cam 35, are closed by the action of face 36 on follower 32.

By the time the bottle has reached the inspection station, which is denoted by the numeral 55, the bottle is clear of input conveyor 50 and has not yet reached the output conveyor 51 so that its bottom surface is unsupported and the bottle is only supported by the penning action of guard 53 and the clamping action of clamp 16.

Various inspections or other operations could be carried out at the station 55, for example, the bottle could be inspected for cleanliness as is illustrated by way of example only in this disclosure.

Inspection for cleanliness is commonly carried out by illuminating the bottom of the bottle with a uniform diffused light source and detecting opaque contaminants by their contrast against the uniform background. The light source and detector illustrated are designated 56 and 57, respectively. The light source is kept on continuously during the operation of the machine but the detector is activated only when the starwheels are indexed such that one of the recesses 14 and 15 are at inspection station 55. The activation of the detector 57 may be accomplished by locating a series of opaque pins 58 on the top surface of starwheel 12 at some convenient radius, one pin 58 being associated with each clamp 16. Photocell 59 and lamp 60 are mounted on bracket 61 in such a way that the photocell is illuminated by the lamp but that the illumination is interrupted by the pins 58 as the starwheel is turned. The location of the bracket 61 is such that as any particular bottle held in a clamp 16 arrives at inspection station 55, the pin 58 associated with that clamp will interrupt the light impinging on the photocell. Circuitry, not shown, but understood by those skilled in the art, activates the detector when the light to photocell 59 is interrupted. Prior art methods of activation are unsatisfactory since they use the bottle itself to interrupt a light beam and transparent bottles may cause no or multiple activations.

If the bottle being inspected is satisfactory with respect to the inspection operation performed, no action is initiated by the detector 57. If, on the other hand, contamination is present in the bottle, a signal from detector 57 energizes solenoid 62 momentarily. Solenoid 62 is mounted on overhanging arm 37 and its armature 63 is attached to pivoted lever 64 which extends through a hole in arm 37. At the moment that the inspection step is accomplished, the cam follower 32 associated with the clamp 16 holding the bottle being inspected is adjacent to the lever 64 and energization of the solenoid causes the lever to push the cam follower sufficiently to cause the clamp actuator 27 to retract enough to cause the toggle joint to assume its other stable state, that is, the clamp opens. As the starwheels continue to turn, a bottle which has been rejected continues to be supported in its recess by the action of guard 53 as previously described. Acceptable bottles are additionally secured by clamp 16.

The guard 53 is so shaped that when a rejected bottle reaches position 65, it is released from the starwheel. The bottle is supported on its bottom by the output conveyor 51 which begins at that point and runs tangent to the rejected bottle corral 67. Guide 66 serves to derail the rejected bottles into the corral while the conveyor runs under the guide and picks up accepted bottles at a point beyond.

It is possible, as an alternative, to introduce a time delay mechanism into the inspection circuitry, a device well known to those skilled in the art, whereby the signal activating solenoid 58 will be delayed the time interval required for a bottle to travel from station 55 to station 65. The solenoid 58, in this alternative, would be located at the station 65 to release rejected bottles at that point for transfer to the rejected bottle corral. Guard 53 would be unnecessary to this embodiment and could be eliminated.

Accepted bottles are not released at position 65 when guard 53 no longer is effective since the clamp 16 still holds the bottle in its grasp. Cam 69 is positioned to engage cam followers 32 of those clamps not open, that is of clamps holding bottles not rejected, when the accepted bottle is aligned with channel 68 formed by guides 66 and 69. The clamp 16 opening at that point releases the bottle. A small auxiliary conveyor system 70 supports the bottom of the accepted bottles which have been released and conveys them, as guided in channel 68, to output conveyor 51. Conveyor 51 conveys the accepted bottles to the next station as required.

The means for supporting and adjusting starwheels 12 and 13 is illustrated in FIGS. 9, 10 and 11. Circular support plate 80 is bolted onto the central shaft 11 with bolt 81. Four chain sprockets 82, 83, 84 and 85 are attached, free to turn, to the support plate 80 and coupled together by chain 86. The sprockets 82, 83 and 84 have their interiors threaded while sprocket 85 has a hexagonal hole through its center. Three threaded rods, of which only one, designated by the numeral 87, can be seen in drawings, are threadedly engaged with the threaded holes in the sprockets and are tightly secured to the upper starwheel support 88. A hexagonal rod 89 is a slip fit into the hexagonal hole of sprocket 85. The upper portion of rod 89 is rotatably mounted on support plate 88. It can be seen then that turning of rod 89 from a position above support plate 88 will cause all of the sprockets to turn and support plate 88 to rise or fall depending on the direction of rotation. Starwheel 12 is concentric with support plate 88 and is bolted to same in a manner which allows the starwheel to be changed easily to one, for example, which accommodates a bottle with a different sized neck. Shield 91 goes up and down with the starwheel and prevents foreign material from entering the adjusting mechanism.

The lower starwheel 13 is supported from support plate 80 by tube 90 and remains in a fixed position vertically. Thus rotation of hexagonal rod 89 allows the spacing between starwheels 12 and 13 to be adjusted to accommodate any desired height bottle. The starwheels themselves may be easily changed so that different shaped bottles may be processed.

What has been disclosed is a novel container handling apparatus. A particular embodiment has been described for purposes of example only and it should be understood that various modifications and changes could be made within the spirit of the invention and within the scope of the appended claims.

I claim:

1. Container conveying apparatus which comprises:
   a. a pair of spaced substantially circular rotatable discs, said discs each having a plurality of recesses on the periphery thereof, said recesses in each of said discs being aligned whereby containers may be held in said recesses;
   b. a plurality of clamps aligned with said recesses whereby containers may be secured in said recesses, each said clamp comprising,
      i. a pair of spaced elongate members, said members being pivoted intermediate the ends thereof, said members extending substantially radially of said discs,
      ii. a toggle joint joining the inboard ends of said spaced members whereby straightening of said toggle joint will cause the outboard ends of said members to approach each other so as to hold a container therebetween,
      iii. means for limiting the motion of said toggle joint, said limit in one direction allowing said clamp to be in an open condition and said limit in the opposite direction being slightly over center of said toggle whereby said clamp is in closed position, and
      iv. a tension spring joining the inboard portions of said spaced members whereby said clamp will have two stable positions,
   c. means for causing each of said clamps to close upon said clamp passing a first predetermined position; and
   d. means for causing each of said clamps to open upon said clamp passing a second predetermined position whereby a container held in said recess will be delivered at a first output position.

2. Container conveying apparatus as recited in claim 1 and further including a cam follower secured to said toggle joint on each of said clamps and wherein said means for causing said clamps to open and to close comprises a pair of cams.

3. Container conveying apparatus as recited in claim 2 and further including
   a. means for identifying said containers as belonging to one of a plurality of possible classes;
   b. means for causing any of said clamps holding a container belonging to the first of said classes to release said container at a third predetermined position, said third predetermined position being intermediate said first and said second predetermined positions whereby said containers belonging to said first class will be delivered at a second output position.

4. Container conveying apparatus as recited in claim 3 and further including additional securing means, said additional securing means securing said containers in said recesses between said third predetermined position and said second output position.

5. Container conveying apparatus as recited in claim 4 wherein said additional securing means comprises a guard rail surrounding a portion of the periphery of said pair of discs.

6. Container conveying apparatus as recited in claim 3 wherein said means for causing said clamps to release said containers includes a solenoid disposed to deliver an impulse to said cam follower.

7. Container conveying apparatus which comprises:
   a. a pair of spaced substantially circular rotatable discs, said discs each having a plurality of recesses on the periphery thereof, said recesses in each of said discs being aligned whereby containers may be held in said recesses;
   b. a plurality of clamps aligned with said recesses whereby containers may be secured in said recesses;
   c. means for causing each of said clamps to close upon said clamp passing a first predetermined position;
   d. means for causing each of said clamps to open upon said clamp passing a second predetermined position whereby a container held in said recess will be delivered at a first output position; and
   e. means for identifying said containers as belonging to one of a plurality of possible classes; and
   f. means for causing any of said clamps holding a container belonging to the first of said classes to release said container at a third predetermined position, said third predetermined position being intermediate said first and said second predetermined positions whereby said containers belonging to said first class will be delivered at a second output position.

8. Container conveying apparatus as recited in claim 7 and further including additional securing means, said additional securing means securing said containers in said recesses between said third predetermined position and said second output position.

9. Container conveying apparatus as recited in claim 8 wherein said additional securing means comprises a guard rail surrounding a portion of the periphery of said pair of discs.

10. Container conveying apparatus as recited in claim 9 and further including means for actuating said identifying means when said containers are in predetermined positions which comprises:
    a. a plurality of opaque obstructions protruding from one of said discs, there being one of said obstructions in predetermined spacial relationship with each of said recesses;
    b. a lamp disposed to illuminate said obstructions as they pass a predetermined position; and
    c. a photoelectric cell within view of said lamp whereby light from said lamp to said photocell will be interrupted by the passage of each of said obstructions.

11. Container conveying apparatus which comprises:
    a. a pair of spaced substantially circular rotatable discs, said discs each having a plurality of recesses on the periphery thereof, said recesses in each of said discs being aligned whereby containers may be held in said recesses;
    b. a plurality of clamps aligned with said recesses whereby containers may be secured in said recesses;
    c. means for causing each of said clamps to close upon said clamp passing a first predetermined position;
    d. means for causing each of said clamps to open upon said clamp passing a second predetermined position whereby a container held in said recess will be delivered at a first output position;
    e. where said clamps are bistable devices whereby said clamps may be opened or closed by application of an impulse.

12. Container conveying apparatus as recited in claim 11 and further including:
    a. means for identifying said containers as belonging to one of a plurality of possible classes;

b. means for imparting an impulse at a third predetermined position at any of said clamps holding a container belonging to the first of said classes, said third predetermined position being intermediate said first and second predetermined positions whereby said containers belonging to said first class will be delivered at a second output position.

13. Container conveying apparatus as recited in claim 12 and further including additional securing means, said additional securing means securing said containers in said recesses between said third predetermined position and said second output position.

14. Container conveying apparatus as recited in claim 13 wherein said additional securing means comprises a guard rail surrounding a portion of the periphery of said pair of discs.

15. Container conveying apparatus as recited in claim 14 wherein said means for imparting an impulse to said clamps comprises a solenoid activated by said identifying means.

16. Container conveying apparatus as recited in claim 1 wherein said spaced elongate members are slightly flexible whereby they will deflect so as to grasp containers without breakage of said container.

17. Container conveying apparatus as recited in claim 5 wherein said spaced elongate members are slightly flexible whereby they will deflect so as to grasp containers without breakage of said container.

18. A container clamp for a container conveying apparatus comprising:
    a. a support;
    b. a pair of spaced elongate members having first and second ends, said members being pivotally supported by said support between said ends thereof, said members extending in side by side relation and having means adjacent said first ends for engaging a container;
    c. a toggle joint coupling said members adjacent said second ends of said spaced members whereby straightening of said toggle joint will cause said first ends of said members to approach each other so as to hold a container therebetween;
    d. means for limiting the motion of said toggle joint, said limit in one direction allowing said clamp to be in an open condition and said limit in the opposite direction being slightly over center of said toggle whereby said clamp is in a closed position;
    e. a tension spring coupled between said members adjacent to each said second ends thereof whereby said clamp will have two stable positions; and
    f. a cam follower secured to said toggle joint.

19. The container clamp as recited in claim 18 wherein said spaced elongate members are flexible whereby they will deflect so as to grasp containers without breakage of said container.

20. The container clamp as recited in claim 18 wherein said support is a substantially horizontal member.

21. A container clamp for a container conveying apparatus comprising:
    a. a support;
    b. a pair of spaced elongate members having first and second ends, said members being pivotally supported by said support between said ends thereof, said members extending in side by side relation and having means adjacent said first ends for engaging a container;
    c. a toggle joint coupling said members adjacent said second ends of said spaced members whereby straightening of said toggle joint will cause said first ends of said members to approach each other so as to hold a container therebetween;
    d. means for limiting the motion of said toggle joint, said limit in one direction allowing said clamp to be in an open condition and said limit in the opposite direction being slightly over center of said toggle whereby said clamp is in a closed position;
    e. a tension spring coupled between said members adjacent to each said second ends thereof whereby said clamp will have two stable positions;
    f. said support is a circular rotatable disc having a plurality of recesses on the periphery thereof, said recesses being arranged and configured whereby said containers may be held in said recesses by said elongated members.

22. The container clamp as recited in claim 18 wherein said pair of spaced elongated members are disposed in a horizontal plane.

23. The container clamp as recited in claim 21 wherein said pair of spaced elongated members are cooperatively disposed on said support adjacent said recesses whereby said clamp may retain a container adjacent said recesses when said elongated members are in said closed position.

24. The container clamp as recited in claim 21 wherein said means for engaging a container includes means for encouraging a container into a predetermined position with respect to a respective recess.

25. A container engaging clamp comprising:
    first and second members moveable between first and second relative stable positions, said first and second members having means for engaging and encouraging a container into a predetermined position when in said first relative position;
    toggle means coupled to said first and second members for retaining said first and second members in said first position, said toggle means including means for limiting the motion of said toggle means in one direction to a slightly over center condition to retain said first and second members in said first relative position; and
    a cam follower coupled to said toggle means.

26. The container engaging clamp of claim 25 wherein said means for engaging a container is coupled to the ends of said first and second members.

27. The container engaging clamp of claim 25 wherein said first and second members are flexible members to yieldably engage the containers.

28. A container clamp comprising:
    a support;
    first and second generally elongate members, said elongate members having means for engaging containers adjacent a first end thereof, said elongate members each being rotatably mounted to said support between its two respective ends so that said members may rotate to vary the separation of said first ends;
    an actuating member moveable between first closed and second open positions with respect to said support;
    first and second coupling members, each of said coupling members being rotationally coupled adjacent one end to said actuating member and rotationally coupled adjacent the other end to a respective one of said generally elongate members, said actuating member having a position adjacent said first position whereby the axes of rotational coupling of said first and second members are in a plane, thereby creating an over center condition in said first position;

means coupled to each said first and second elongate members encouraging said elongated members to remain in said first closed position and in said second open position; and a cam follower supported by said actuating member.

29. The container clamp of claim 28 wherein said means coupled to each said first and second elongated members is a spring.

30. The container clamp of claim 28 wherein said generally elongate members are flexible plastic members so as to yieldably grasp said containers.

31. The container clamp of claim 28 wherein said support is a substantially horizontal member.

32. A container clamp comprising:

a support;

first and second generally elongate members, said elongate members having means for engaging containers adjacent a first end thereof, said elongate members each being rotatably mounted to said support between its two respective ends so that said members may rotate to vary the separation of said first ends;

an actuating member moveable between first closed and second open positions with respect to said support;

first and second coupling members, each of said coupling members being rotationally coupled adjacent one end to said actuating member and rotationally coupled adjacent the other end to a respective one of said generally elongate members, said actuating member having a position adjacent said first position whereby the axes of rotational coupling of said first and second members are in a plane, thereby creating an over center condition in said first positions; and means coupled to each said first and second elongate members encouraging said elongated members to remain in said first closed position and in said second open position;

wherein said support is a circular rotatable disc having a plurality of recesses on the periphery thereof, said recesses being arranged and configured whereby said containers may be held in said recesses.

33. The container clamp of claim 28 wherein said first and second elongated members are disposed in a horizontal plane and formed to encourage a container into a respective recess when in said first closed position.

34. A container clamp comprising:

a support;

first and second grasping members, said members being moveable on said support between a closed first position and an open second position, said first and second members having means for engaging a container when in said first position;

first and second coupling members, said coupling members rotationally coupled adjacent to one end of each of said first and second grasping members, said coupling members moveable between said closed first position and said second open position;

means for yieldably encouraaging said grasping member in said first closed position and second open positions; and cam follower means coupled to said coupling members.

35. The container clamp of claim 34 wherein said support is a circular rotatable disc having a plurality of recesses on the periphery thereof, said recesses being arranged and configured whereby said containers may be held in said recesses, and wherein said means for engaging a container include means for encouraging a container into a predetermined position with respect to a respective recess disposed in said support.

36. The clamp of claim 34 wherein said means for yieldably encouraging said grasping means is coupled to each said first and second grasping member adjacent the ends thereof.

37. The clamp of claim 36 wherein said means for yieldably encouraging said grasping members is a tension spring.

38. The clamp of claim 34 wherein said grasping means are disposed in a horizontal plane.

* * * * *